(12) United States Patent
Takahashi et al.

(10) Patent No.: US 7,767,877 B2
(45) Date of Patent: Aug. 3, 2010

(54) LIQUID-ABSORBING CORE

(75) Inventors: Masatoshi Takahashi, Tokyo (JP); Kanji Mizunaka, Tokyo (JP)

(73) Assignee: S.T. Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/485,434

(22) PCT Filed: Aug. 3, 2001

(86) PCT No.: PCT/JP01/06690

§ 371 (c)(1),
(2), (4) Date: Mar. 15, 2004

(87) PCT Pub. No.: WO03/013619

PCT Pub. Date: Feb. 20, 2003

(65) Prior Publication Data

US 2004/0243077 A1   Dec. 2, 2004

(51) Int. Cl.
*A61F 13/15* (2006.01)
*A61M 16/00* (2006.01)
*A61J 15/00* (2006.01)
*A61L 9/00* (2006.01)

(52) U.S. Cl. .............. 604/367; 604/385.01; 392/390; 239/44; 422/4

(58) Field of Classification Search .......... 604/385.01, 604/366, 367, 374, 375, 378; 392/390–395; 239/44; 422/4, 122–126
See application file for complete search history.

(56) References Cited

U.S. PATENT DOCUMENTS

| | | | | |
|---|---|---|---|---|
| 3,903,889 A | * | 9/1975 | Torr | 604/365 |
| 5,038,394 A | * | 8/1991 | Hasegawa et al. | 392/395 |
| 5,647,053 A | * | 7/1997 | Schroeder et al. | 392/390 |
| 6,403,857 B1 | * | 6/2002 | Gross et al. | 604/365 |
| 6,562,294 B1 | * | 5/2003 | Smith | 422/5 |
| 6,766,817 B2 | | 7/2004 | da Silva | |
| 2002/0136886 A1 | * | 9/2002 | He et al. | 428/313.5 |

FOREIGN PATENT DOCUMENTS

| | | |
|---|---|---|
| JP | 63-283647 | 11/1988 |
| JP | 05-277172 | 10/1993 |
| JP | 5-328884 | 12/1993 |
| JP | 8-131045 | 5/1996 |
| JP | 9-158027 | 6/1997 |
| JP | 11-197228 | 7/1999 |
| JP | 11-332971 | 12/1999 |

* cited by examiner

*Primary Examiner*—Jacqueline F. Stephens
(74) *Attorney, Agent, or Firm*—Jordan and Hamburg LLP

(57) ABSTRACT

A liquid-absorbing core which is for use in suction type drug volatilizers which comprises hydrophilic fibers and/or water-absorbing fibers. The hydrophilic fibers have an affinity for water, and are rayon, cotton, etc. Especially preferred is rayon because it has a high affinity for water. Examples of the water-absorbing fibers include water-absorbing synthetic fibers made of a polymer such as polyvinyl alcohol or polysodium acrylate and other synthetic fibers treated by, e.g., adding and adhering polyvinyl alcohol or polysodium acrylate thereto or coating them with the polymer. In the liquid-absorbing core, the hydrophilic fibers and/or water-absorbing fibers may be disposed so as to have a porosity of 10 to 80%.

18 Claims, 1 Drawing Sheet

LIQUID-ABSORBING CORE

TECHNICAL FIELD

The present invention relates to a liquid-absorbing core used in an absorption-type chemical agent vaporization apparatus.

BACKGROUND ART

Absorption-type chemical agent vaporization apparatuses that absorb chemical solutions such as aromatic substances, deodorants, insect repellents, and pesticides by means of liquid-absorbing cores, members for absorption, and diffuse them in the environment have conventionally been provided. The liquid-absorbing cores are synthetic fibers such as polyester, polypropylene and acetate blended with heat-fusible fibers and formed into pillars, that lead chemical solutions contained in the containers to the mouths of the containers through capillary action. The chemical solutions lead to the mouths of containers develop into fumes that diffuse to provide the environment with the effects of chemical agents.

In order to meet the increasing economic mind of consumers, the volume tends to increase recently and absorption-type chemical agent vaporization apparatuses with containers that are larger and taller than before are under development. When a conventional liquid-absorbing core is used for this tall container, the chemical solution can be absorbed up and diffused to the environment without trouble during initial stage of use when the container is filled with the chemical solution up to the top (high position). When the chemical solution is reduced after being used for a while and left only at the bottom of the container, however, the force of absorption is not enough to lead the chemical solution up to the mouth of the container. Therefore, diffusion stops although the chemical solution is left, resulting in a problem that performance of a large chemical solution diffusion apparatus cannot be fully exerted.

The present invention has been done in view of such a problem, and aims at providing a liquid-absorbing core that leads the chemical solution to the last drop up to the mouth of the container to diffuse it even when a tall large container is used.

DISCLOSURE OF THE INVENTION

In order to solve the problems described above, the present invention provides a liquid-absorbing core comprising hydrophilic fiber and/or water-absorbing fiber.

The hydrophilic fiber used for the present invention is a fiber having affinity to water such as rayon, cotton and pulp. Rayon is preferably used because of particularly high affinity to water and good processability that enables easy formation of the liquid-absorbing core in the predetermined shape helped by its length.

Further, water-absorbing synthetic fibers such as polyvinylalcohol and sodium polyacrylate, and other synthetic fibers treated with polyvinylalcohol or sodium polyacrylate by adhesion or coating can be mentioned as the water-absorbing fibers used for the present invention. As a commercial product, "Lanseal" (from Toyobo) can be mentioned.

The liquid-absorbing core of the present invention may have voidage of hydrophilic fiber and/or water-absorbing fiber of 10% to 80%. Voidage of over 80% leaves too large openings to absorb the chemical solutions high enough, and that of less than 10% reduces the amount of the chemical solution absorbed up and non-volatile ingredients (such as surfactants and dyes) fill the openings so that upward absorption of the chemical solutions may stop.

The liquid-absorbing core of the present invention can be obtained by simply bundling hydrophilic fiber and/or water-absorbing fiber, or by weaving them into threads or strings. Also, the bundles of hydrophilic fiber and/or water-absorbing fiber can be rolled with films or tapes of polyethylene, polypropylene or cellophane to form pillars.

Further, the liquid-absorbing core of the present invention is formed by blending hydrophilic fiber and/or water-absorbing fiber with heat-fusible fiber and heat-fusing the same.

Polyethylene, polypropylene, low melting point polyester, and core-sheath fiber of PET/PE can be mentioned as the heat-fusible fibers used for the present invention. Among them, low melting point polyester with a wide range of heat fusion temperature is preferably used in view of heat-fusibility and productivity.

Conventionally known methods can be used for blending hydrophilic fiber and/or water-absorbing fiber with heat-fusible fiber. The blended fibers can be molded into desired shapes by conventionally known methods. The ratio of blending of hydrophilic fiber and/or water-absorbing fiber with heat-fusible fiber can be selected within the ranges of 95% to 15% of the hydrophilic fiber and/or the water-absorbing fiber and 5% to 85% of the heat-fusible fiber. Less than 5% of the heat-fusible fiber causes difficulty in formation of the liquid-absorbing core, and over 85% of it reduces the effect of upward absorption of the liquid.

Further, the present invention provides a liquid-absorbing core molded into pillars by gluing hydrophilic fiber and/or water-absorbing fiber with an adhesive. Polyurethane resin and epoxy resin can be mentioned as the adhesive.

Also, another synthetic fiber can be blended in the present invention for the purpose of prevention of fuzz and improvement of moldability. Moldability here means reduction of frictional resistance with the molding machine for improvement of smoothness of extrusion in extrusion molding of the liquid-absorbing core of the present invention.

Polyester and nylon can be mentioned as the synthetic fibers used in the present invention. The ratio of the synthetic fiber to be blended is up to 80% of the whole composition of the core. The ratio of over 80% prevents exertion of the effect of high absorption of the liquid even though smoothness of extrusion may be obtained.

The liquid-absorbing core of the present invention can be used in conventionally known absorption-type chemical agent diffusion apparatuses. In other words, the chemical solution is placed in a container equipped with an opening mouth, and a liquid-absorbing core of the present invention is positioned to reach from the mouth to the bottom of the container that leads the chemical solution in the container to the mouth through a capillary action. The chemical solution led to the mouth develops into volatile that volatilizes to provide the environment with effects of chemical agent.

Use of the liquid-absorbing core of the present invention in such an absorption-type chemical agent diffusion apparatus enables the apparatus to lead the chemical solution to the above-mentioned mouth even when the amount of the chemical solution is reduced and the solution is left only at the bottom of a tall container that conventionally does not allow absorption of liquid to the top.

BEST MODE FOR CARRYING OUT THE INVENTION

Figure 1:
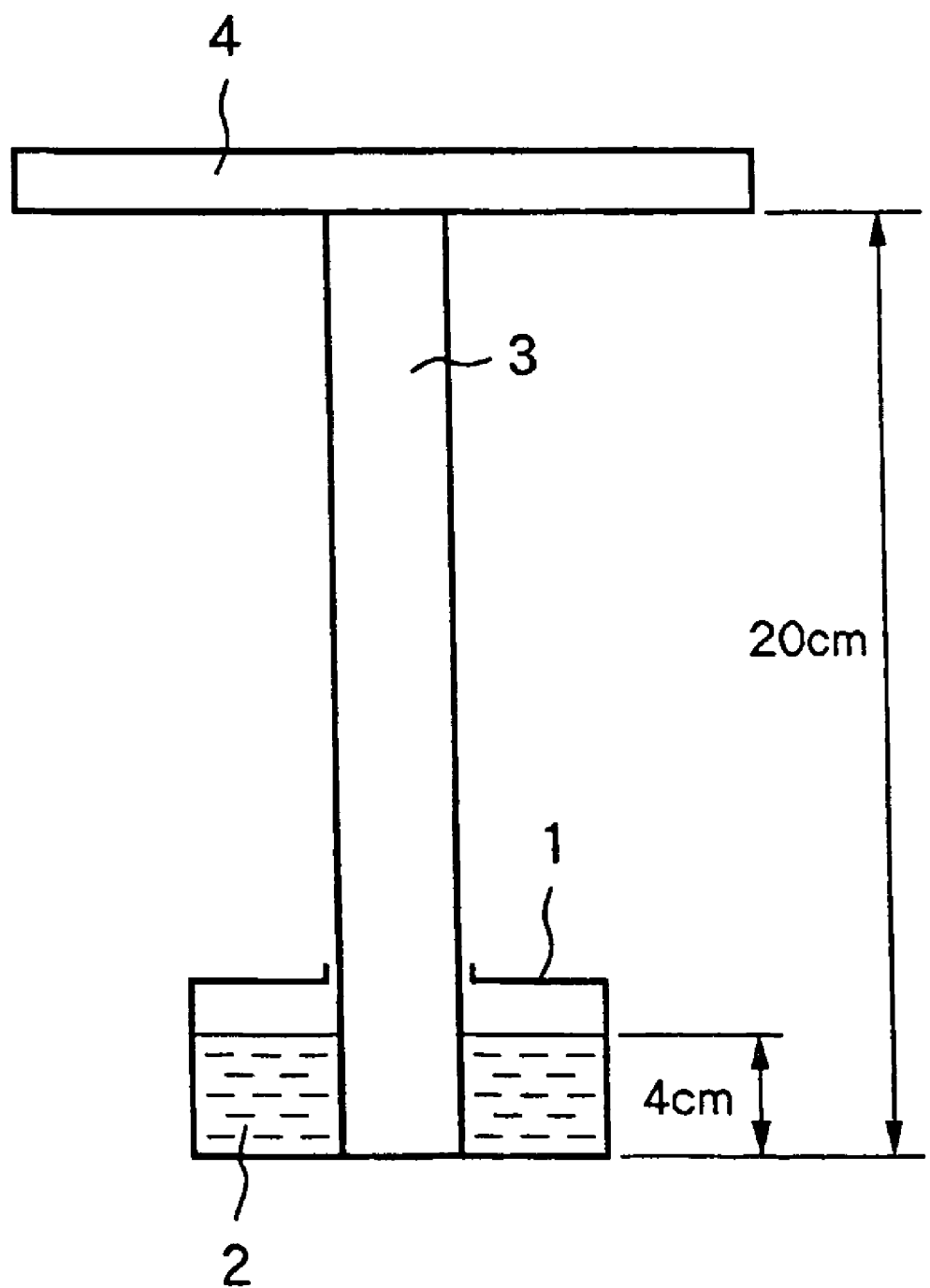
FIG. 1 is a schematic view of the absorption test method.

For explaining the present invention in more detail, explanation will be made hereinbelow with reference to the accompanying drawings. The voidage described above is calculated by the following equation.

$$\text{Voidage (\%)} = \frac{\pi r^2 \times L - \frac{g}{\rho}}{\pi r^2 L} \times 100 \qquad \text{[Equation 1]}$$

r: radius of the liquid-absorbing core (cm)
L: length of the liquid-absorbing core (cm)
g: weight of the liquid-absorbing core (g)
$\rho$: specific gravity of the fiber (g/cm$^3$)

$\rho = \rho_1 1 + \rho_2 2 + \ldots \rho_n n$ $\rho_{1-n}$: density of fiber 1–n
1–n: ratio of blending of fiber 1–n

EXAMPLE 1

Polyester 3 kg as a synthetic fiber, rayon 4 kg as water absorbing fiber, and low melting point polyester 3 kg were carded with a carding machine to obtain tops. Eight tops obtained were drawn several times with a leveler to obtain slivers. The sliver thus obtained was sent through a cylindrical heater heated at 230 to 240° C. and then through a cooling nozzle to obtain a 4φ thick liquid-absorbing core. The voidage of this liquid-absorbing core was 60%. The liquid-absorbing core of this example thus obtained and cut to the length of 20 cm absorbed a solution of an aromatic substance up to the top when its lower end was dipped in it.

EXAMPLE 2

Rayon fiber was weaved into strings to prepare a liquid-absorbing core. The voidage of this liquid-absorbing core was 70%. The liquid-absorbing core of this example thus obtained and cut to the length of 20 cm absorbed a solution of an aromatic substance up to the top when its lower end was dipped in it.

EXAMPLE 3

"Lanseal", trade name, (a product of Toyobo) was carded with a carding machine to obtain tops. Four tops thus obtained were drawn several times with a leveler to obtain slivers. The slivers obtained were wound with polypropylene tape to prepare a pillar-shaped liquid-absorbing core. The voidage of the liquid-absorbing core was 30%. The liquid-absorbing core of this example thus obtained and cut to length of 20 cm absorbed an aqueous solution of an aromatic substance up to the top, when its lower end was dipped in it.

EXAMPLE 4

Cotton 5 kg and polyester 5 kg were carded with a carding machine to obtain tops. Six tops thus obtained were drawn several times with a leveler to obtain slivers. The slivers obtained were dipped in a polyurethane adhesive bath, squeezed to get rid of excessive adhesive, and left standing to obtain a liquid-absorbing core. The voidage of the liquid-absorbing core was 20%. The liquid-absorbing core of this example thus obtained and cut to length of 20 cm absorbed an aqueous solution of an aromatic substance up to the top, when its lower end was dipped in it.

EXAMPLE 5

Rayon was carded with a carding machine to obtain tops. Eight tops thus obtained were drawn several times with a leveler to obtain slivers. The slivers obtained were sent through a blow-molding machine for polyethylene to inject polyethylene around the wall of the slivers. This was sent through a water bath for cooling to obtain a pillar-shaped liquid-absorbing core. The voidage of the liquid-absorbing core was 80%. The liquid-absorbing core of this example thus obtained and cut to length of 20 cm absorbed an aqueous solution of an aromatic substance up to the top, when its lower end was dipped in it.

EXAMPLE 6

Pulp 5 kg and low melting point polyester 5 kg were thoroughly mixed and flattened to form a 10 cm thick sheet, that was sent through a hot roller heated at 230° C. to 240° C. to obtain a 1 cm thick sheet. The voidage of the sheet thus obtained was 30%. This sheet was cut into a 1 cm wide by 20 cm long piece to obtain a square pillar-shaped liquid-absorbing core of the present invention. The liquid-absorbing core of this example thus obtained absorbed an aqueous solution of an aromatic substance up to the top, when its lower end was dipped in it.

EXAMPLES 1-1 THROUGH 1-7

Examples 1-1 through 1-7 and Comparative examples 1 and 2 are shown in Table 1 below. In Examples 1-1 through 1-7 and Comparative Examples 1 and 2, liquid-absorbing cores were obtained in the same manufacturing steps as in Example 1 described above, and with examples of blending ratios (in % by weight) shown in Table 1 below. Voidages in these Examples 1-1 through 1-7 and Comparative examples 1 and 2 were all 60%.

Absorption tests were carried out with a configuration shown in FIG. 1. In other words, an aromatic deodorant solution 2 was placed up to 4 cm from the bottom of a container 1. A liquid-absorbing core 3 of each example 1-1 through 1-7 and comparative examples 1 and 2 was cut to a length of 20 cm, the lower end of each liquid-absorbing core was inserted through the mouth into the container 1, and a 9 cm$^2$ wide filter paper 4 was placed on its upper end. After being left standing for ah hour, infiltration of the aromatic deodorant solution 2 into the filter paper 4 was observed visually. The absorption tests in which the aromatic deodorant solution 2 reached the filter paper 4 were given "○", and those in which the solution failed to reach the filter paper 4 were given "x". Concerning "moldability", the tests in which the liquid-absorbing cores could be formed in the same manufacturing steps as in example 1 described above were given "○".

TABLE 1

|  |  | Example 1-1 | Example 1-2 | Example 1-3 | Example 1-4 | Example 1-5 | Example 1-6 | Example 1-7 | Comparative example 1 | Comparative example 2 |
|---|---|---|---|---|---|---|---|---|---|---|
| Hydrophilic fiber | Rayon | 15 | 95 | 15 | 30 |  |  |  |  |  |
|  | Cotton |  |  |  |  | 30 |  |  |  |  |
| Water-absorbing fiber | Lanseal |  |  |  |  |  | 30 |  |  |  |
|  | Polyvinylalcohol |  |  |  |  |  |  | 30 |  |  |
| Heat-fusible fiber | Low melting point polyethylene | 85 | 5 | 5 | 50 | 40 | 40 | 40 | 40 | 5 |
| Synthetic fiber | PET |  |  | 80 | 20 | 30 | 30 | 30 | 60 | 95 |
| Moldability |  | ○ | ○ | ○ | ○ | ○ | ○ | ○ | ○ | ○ |
| Absorption |  | ○ | ○ | ○ | ○ | ○ | ○ | ○ | x | x |

* Lanseal, ultra-water-absorbing fiber (from Toyobo)

As seen in Table 1 shown above, Examples 1-1 through 1-5 comprising rayon or cotton that are hydrophilic fibers and Examples 1-6 and 1-7 comprising PVA-glued PET or polyvinylalcohol that are water-absorbing fibers were given "○" for both "moldability" and "absorption". On the other hand, Comparative examples 1 and 2 without hydrophilic fiber or water-absorbing fiber were given "x" for absorption while they were given "○" for moldability.

Thus, comprising hydrophilic fiber or water-absorbing fiber was confirmed to exert the effect of absorbing liquid high above.

EXAMPLES 1-8 AND 1-9

Examples 1-8 and 1-9 and comparative Example 3 are shown in Table 2 below. In examples 1-8 and 1-9 and comparative example 3, liquid-absorbing cores were obtained in the same manufacturing steps as in Example 1 described above, and with examples of blending ratios (in % by weight) shown in Table 1 below. Voidage was calculated by the same equation shown above and "absorption" was similarly evaluated using a similar test apparatus as in Table 1 shown above.

TABLE 2

|  |  | Example 1-8 | Example 1-9 | Comparative example 3 |
|---|---|---|---|---|
| Hydrophilic fiber | Rayon | 30 | 30 | — |
| Heat-fusible fiber | Low melting point PET | 30 | 30 | 40 |
| Synthetic fiber | PET | 40 | 40 | 60 |
| Voidage |  | 10 | 80 | 10 |
| Absorption |  | ○ | ○ | x |

As seen from Table 2 above, Examples 1-8 and 1-9 comprising hydrophilic fiber, rayon, with voidage of 10% and 80% respectively were given "○" for "absorption". On the other hand, Comparative examples 1 and 2 not comprising hydrophilic fiber or water-absorbing fiber were given "x" for "absorption" while they were given "○" for "moldability".

Thus, comprising rayon was confirmed to exert the effect of absorbing liquid high above. Voidage of 10% to 80% was also confirmed to exert the effect of absorbing liquid high above.

INDUSTRIAL APPLICABILITY

As explained above, the liquid-absorbing core of the present invention exerts the effect of absorbing liquid high above. Therefore, when an absorption-type chemical solution diffusion apparatus using a container that is larger and taller than conventional ones is used, sufficient absorption force can be secured to enable leading chemical solutions to the mouth of the container, even when only a small amount of the chemical solution is left as period of use passed, and the chemical solution is left only at the bottom of the container. Therefore, the chemical solution can be lead to the last drop up to the mouth of the container to diffuse.

Also, good processability can be secured during molding by using rayon, and further, fuzz of liquid-absorbing core can be prevented and moldability can be improved by blending with synthetic fiber.

The invention claimed is:

1. A liquid-absorbing pillar-shaped core being formed by blending non-heat-fusible hydrophilic fibers and/or water-absorbing fibers with heat-fusible fibers comprised of heat-fusible material in a manner forming a fiber blend in which said hydrophilic fibers and/or said water-absorbing fibers and said heat-fusible fibers are thoroughly mixed with one another, and heat-fusing said fiber blend throughout said pillar-shaped core so as to form said heat fusible fibers into an integrally-fused mass of the heat-fusible material throughout which said hydrophillic fibers and/or said water-absorbing fibers are encapsulated, said pillar-shaped core comprising 95% to 15% of said hydrophilic and/or water absorbing fibers and 5 to 85% of said heat-fusible fibers.

2. The liquid-absorbing core according to claim 1, further comprising synthetic fibers blended with said hydrophilic and/or water-absorbing fibers and heat-fusible fibers, said liquid-absorbing core comprising up to 80% of said synthetic fibers.

3. The liquid-absorbing pillar-shaped core according to claim 2, wherein said synthetic fibers comprise at least one of nylon or a second polyester.

4. The liquid-absorbing pillar-shaped core according to claim 2, wherein
said heat-fusible fibers comprise at least one of polyethylene, polypropylene, or a first polyester; and
said synthetic fibers comprise at least one of nylon or a second polyester, said first polyester having a lower melting point than said second polyester.

5. The liquid-absorbing pillar-shaped core according to claim 1, wherein said hydrophilic fibers and/or water-absorbing fibers comprise hydrophilic fibers, said hydrophilic fibers comprising at least one of rayon, cotton, or pulp.

6. The liquid-absorbing pillar-shaped core according to claim 5, wherein said hydrophilic fibers comprise rayon.

7. The liquid-absorbing pillar-shaped core according to claim 1, wherein said hydrophilic fibers and/or water-absorbing fibers comprise water-absorbing fibers, said water-absorbing fibers comprising at least one of polyvinylalcohol or sodium polyacrylate.

8. The liquid-absorbing pillar-shaped core according to claim 1, wherein said liquid-absorbing pillar-shaped core has a voidage of 10% to 80%.

9. The liquid-absorbing pillar-shaped core according to claim 1, wherein said heat-fusible fibers comprise at least one of polyethylene, polypropylene, or a first polyester.

10. A liquid-absorbing pillar-shaped core formed by thoroughly mixing an adhesive with hydrophilic fibers and/or water-absorbing fibers, said hydrophilic fibers being arranged with longitudinal extents thereof codirectional with a length dimension of the liquid-absorbing pilar-shaped core comprised thereof to form an integral mass of glue throughout which said hydrophillic fibers and/or said water-absorbing fibers are encapsulated.

11. The liquid-absorbing pillar-shaped core according to claim 10, further comprising synthetic fibers, said liquid-absorbing core comprising up to 80% of said synthetic fibers.

12. The liquid-absorbing pillar-shaped core according to claim 11, wherein said adhesive comprises at least one of polyurethane resin or epoxy resin.

13. The liquid-absorbing pillar-shaped core according to claim 11, wherein said synthetic fibers comprise at least one of nylon or a second polyester.

14. The liquid-absorbing pillar-shaped core according to claim 10, wherein said hydrophilic fibers and/or water-absorbing fibers comprise hydrophilic fibers, said hydrophilic fibers comprising at least one of rayon, cotton, or pulp.

15. The liquid-absorbing pillar-shaped core according to claim 14, wherein said hydrophilic fibers comprise rayon.

16. The liquid-absorbing pillar-shaped core according to claim 10, wherein said hydrophilic fibers and/or water-absorbing fibers comprise water-absorbing fibers, said water-absorbing fibers comprising at least one of polyvinylalcohol or sodium polyacrylate.

17. The liquid-absorbing pillar-shaped core according to claim 10 comprising at least one of polyurethane resin or epoxy resin as adhesives for said gluing.

18. The liquid-absorbing pillar-shaped core according to claim 10, wherein said liquid-absorbing pillar-shaped core has a voidage of 10% to 80%.

* * * * *